United States Patent [19]
Blacker et al.

[11] Patent Number: 6,087,137
[45] Date of Patent: Jul. 11, 2000

[54] PREPARATION OF HYDROXY COMPOUNDS BY BIOCONVERSION WITH DIOXYGENASE

[75] Inventors: Andrew John Blacker, Leeds; Derek Raymond Boyd, Belfast; Howard Dalton, Long Itchington; Nigel Bowers, Country Down, all of United Kingdom

[73] Assignee: Zeneca Limited, London, United Kingdom

[21] Appl. No.: 08/945,695

[22] PCT Filed: May 20, 1996

[86] PCT No.: PCT/GB96/01208

§ 371 Date: Nov. 21, 1997

§ 102(e) Date: Nov. 21, 1997

[87] PCT Pub. No.: WO96/37628

PCT Pub. Date: Nov. 28, 1996

[30] Foreign Application Priority Data

May 27, 1995 [GB] United Kingdom .................. 9510836
Jun. 6, 1995 [GB] United Kingdom .................. 9-511370

[51] Int. Cl.$^7$ ............................ C12P 17/16; C12P 17/00; C12P 17/10; C12P 7/02
[52] U.S. Cl. ......................... 435/118; 435/117; 435/121; 435/155
[58] Field of Search .................................... 435/155, 128, 435/129, 117, 121, 126, 120, 118

[56] References Cited

PUBLICATIONS

Mitrochkine et al: Synthesis of Enantiomerically Pure (1S, 2R)–Epoxy Indane and cis–(1R,2S)–2–Amino–1–indanol. Tetrahedron Asymmetry vol. 6, No. 1, pp 59–62, 1995 XP002014730, see the whole document.
Boyd et al: "Structures and Stereochemical Assignments of Some Novel Chiral Synthons Derived from the Biotransformation of 2,3–Dihydrobenzofuran and benzofuran by Pseudomonas putida", Tetrahedron Asymmetry vol. 4, No. 6, pp 11307–1324 1993, XP002014731 see the whole document.
Chemical Abstracts, vol. 122, No. 13, Mar. 27, 1995, abstract No. 155016, Resnick et al: "Regiospecific and stereoselective hydroxylation of 1–indanone and 2–indanone by naphthalene dioxygenase and toluene dioxygenase", XP002014734 see abstract & Appl. Environ.Microbiol.(1994),60(9),3323–8.
Chemical Abstracts, vol. 117, No. 23, Dec. 7, 1992, abstract No. 229878, Brand et al: "Stereospecific hydroxylation of indan by *Escherichia coli* containing the cloned toluene dioxygenae genes from Pseudomonas putida F1", XP002014735, see abstract & Appl Environ. Microbiol.(1992)58(10),3407–9 Coden: AEMIDF; ISSN:0099–2240.
Computer Caplus 1983:160361 Boyd et al J. Chem Soc. Perkin Trans. 1 (1982) (11) pp 2767–70, 1983.
J. Chem Soc., Chem.Commun. (1995), (2), 117–18 Coden-:JCCCAT;ISSN: 0022–4936, 1995, XP002014732. Allen et al:"Enntioselective bacterial biotransformation routes to cis– diol metabolites of monosubstituted benzenes, naphtalene and benzocycloalkenes of either absolute configuration" see the wole document.
J. Chem So., Chem Commun. (1989), (6), 339–40 Coden: JCCCAT;ISSN: 0022–4936, 1989, XP002014733, Boyd et al: "Stereospecific bensylic hydroxylation of bicyclic alkenes ny Pseudomonas putida: isolation of (+)–R–1–hydroxy–1,2–dihydronaphthalene, an arene hydrate of naphthalene from metabolism of 1,2–dihydronaphthalene" see the whole document.

*Primary Examiner*—Herbert J. Lilling
*Assistant Examiner*—Jon P. Weber
*Attorney, Agent, or Firm*—Pillsbury Madison & Sutro, LLP

[57] ABSTRACT

A process for preparing a compound of Formula (3) in which $R^2$ is —H;

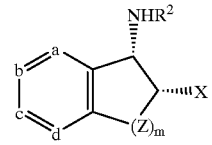

Formula (3)

which comprises the steps:

i) conversion of a compound of Formula (1) into a compound of Formula (2) using a dioxygenase enzyme;

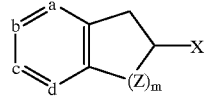

Formula (1)

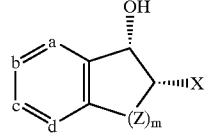

Formula (2)

ii) conversion of the compound of Formula (2) into a compound of Formula (3) wherein is —COR; and
iii) conversion of the compound of Formula (3) in which $R^2$ is —COR into a compound of Formula (3) in which $R^2$ is —H;
wherein $R^2$, a, b, c, d, Z, m and X are as defined in claim 1.

Also claimed are individual steps of the process and new compounds of Formula (2).

9 Claims, No Drawings

PREPARATION OF HYDROXY COMPOUNDS BY BIOCONVERSION WITH DIOXYGENASE

This application is the national phase of international application PCT/GB96/01208, filed May 20, 1996 which designated the U.S.

This invention relates to a process for preparing optically active compounds, e.g. 1-hydroxy-2-substituted indans, and to a process for converting these compounds into the corresponding amido and amino compounds. These optically active compounds are valuable intermediates for synthesis of biologically active pharmaceuticals and agrochemicals, for example inhibitors of enzymes involved in human immunodeficiency virus (HIV) infection such as L-735,524 of Merck and Co. Inc. and novel analogues thereof.

According to a first aspect of the present invention there is provided a process for conversion of a compound of the Formula (1):

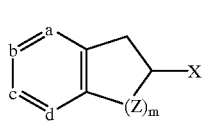

Formula (1)

into a compound of the Formula (2):

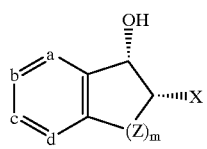

Formula (2)

using a dioxygenase enzyme;
wherein:
a, b, c and d are each independently selected from CH and CY, or one of a, b, c and d is a nitrogen atom and all of the others are selected from CH and CY;
Z is $CH_2$, CHR, $CRR^1$, O, NH, NR, S, C=O or CHX;
X and each Y independently is a substituent other than H;
R and $R^1$ are each independently alkyl, aryl or aralkyl; and
m has a value of from 0 to 4.

The dioxygenase enzyme is preferably a naphthalene dioxygenase enzyme or, more preferably, a toluene dioxygenase enzyme. The dioxygenase enzyme may be in any form capable of converting a compound of Formula (1) into a compound of Formula (2), for example in the form of a cell-free extract, a synthetic form, disintegrated cells or, preferably, the dioxygenase enzyme is present in whole cells. The dioxygenase enzyme is present in whole cells in various strains of *E. Coli* (e.g. *E. Coli* pKS T11 clone, described in J. Chem. Soc. Chem. Commun. 1995, 119–120, which expresses the toluene dioxygenase gene from *P. putida* NCIMB 11767) and various *Pseudomonas putida* micro-organisms. It is preferred that a compound of Formula (1) is converted into a compound of Formula (2) in the presence of a *Pseudomonas putida* micro-organism, more preferably a mutant strain of *Pseudomonas putida* NCIMB 11680 (deposited Oct. 02, 1981) or NCIMB 11767 (deposited Dec. 13, 1982), especially *Pseudomonas putida* UV4, more especially *Pseudomonas putida* NCIMB 8859 (deposited February 1957, available from the NCIMB Catalogue of Strains). Preparation of mutant strains of *Pseudomonas putida* NCIMB 11680 and NCIMB 11767, including *Pseudomonas putida* UV4, are described in European Patent No. 253,485.

To avoid conversion of the compound Formula (2) to the corresponding compound having a double bond between the carbon atoms to which the OH and X groups are attached the process is preferably performed in the absence of a cis dihydrodiol dehydrogenase enzyme.

*Pseudomonas putida* UV4 and its use are described in a number of publications, e.g. Tetrahedron Letters, vol 32, No. 31, pp 3887–3890 (1991); J. Chem. Soc. Chem. Commun. pp 49–51 (1993); Tetrahedron: Asymmetry Vol. 4, No. 6, pp1307–1324 (1993); J. Chem. Soc., Chem. Commun, pp 974–976, (1993); J. Am. Chem. Soc 116, pp 1147–1148, (1994); and J. Chem. Soc., Chem. Commun., pp 117–118 (1995). However none of these publications describe the valuable process according to the present invention in which compounds of Formula (1) having a 2-substituent are converted to the compounds of Formula (2) having the stereochemistry shown above.

Each X and each Y independently is preferably alkyl, —OH, —OR, —OCOR, —SH, —SR, —F, —Cl, —Br, —I, —$NH_2$, —NHR, —$NRR^1$, —NHCOR, —$NRCOR^1$, —CN, —COOR, —COOH, —COR, —$CONH_2$, —CONHR, —$CONRR^1$, —$NO_2$, —$N_3$, —$PRR^1$, —$P(O)RR^1$, —$P(O)(OH)_2$, —P(O)(OROH), —$P(O)OROR^1$, —S(O)R, —$SO_2R$, —$SO_2H$ or —$SO_3H$; more preferably alkyl, —OH, —OR, —OCOR, —SR, —F, —Cl, —Br, —I, —$NH_2$, —NHR, —$NRR^1$, —CN or —$N_3$; wherein R and $R^1$ are each independently alkyl, aryl or aralkyl.

Preferably a, b, c and d are all selected from CY and CH, more preferably they are all CH, i.e. the 6-membered ring they form part of is a benzene ring.

When Z is $CH_2$, CHR, NH or S it is possible to form derivatives in minor amounts in which one of the H atoms in the Z group is replaced by —OH during the process. For example the compound of Formula

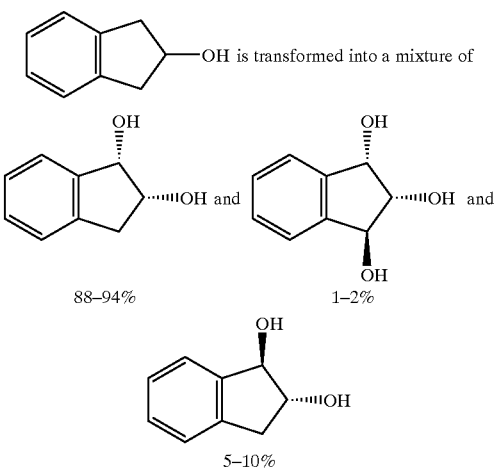

1S-hydroxy-2-ketoindan and 2R-hydroxy-1-ketoindan are formed as minor components.

When any one of R, $R^1$, X, Y or Z is or contains an alkyl the alkyl is preferably $C_{1-10}$-alkyl, more preferably $C_{1-6}$-alkyl and especially methyl. Where either of R or $R^1$ is or contains aryl the aryl is preferably phenyl. Where either of R or $R^1$ is or contains aralkyl the aralkyl is preferably phenyl$C_{1-6}$-alkyl, more preferably phenyl$C_{1-4}$-alkyl and especially benzyl.

Z is preferably CH$_2$.

m is preferably 0, 1, 2, 3 or 4, more preferably 1 or 2.

Especially preferred processes use a compound of Formula (1) which is a 2-substituted indan, especially those in which a, b, c and d are all CH, X is —OH, —OCO(C$_{1-4}$-alkyl), —Cl, —Br, —N$_3$ or CH$_3$; Z is CH$_2$ and m is 1. The compounds of Formula (2) are preferably 2-substituted indan-1-ols.

The process for converting a compound of Formula (1) into a compound of Formula (2) using a dioxygenase enzyme can be regarded as a biotransformation process. The process is preferably carried out in a liquid medium, preferably in an aqueous medium and especially in a buffered aqueous medium. Suitable buffers may be inorganic or organic and are preferably those which control the pH of the medium in the range 6 to 8, more preferably in the range 6.5 to 7.5 and especially at a pH of 7.2. The buffer is preferably inorganic, more preferably an alkali metal phosphate, especially potassium phosphate. An especially preferred buffer is 0.1M potassium phosphate.

The pH of the process may optionally be maintained at a pH of 7.2 by an intermittent feed of a base, preferably an inorganic base, more preferably an alkali metal hydroxide such as dilute aqueous potassium hydroxide.

A co-substrate which provides for NADH recycle may optionally be added to the liquid medium. Preferred co-substrates are α-ketoacids and their alkali metal salts such as pyruvic acid and sodium pyruvate and alcohols such as ethanol, isopropanol or a sugar, e.g. glucose.

The process involves oxidation of the compound of Formula (1) and the source of oxygen is usually molecular oxygen. Thus during the process oxygen is preferably continuously sparged through the liquid medium, for example in the form of air, preferably providing a saturated concentration of oxygen.

The process is preferably performed at a temperature from 0° C. to 100° C., more preferably at from 20° C. to 45° C. and especially at from 28° C. to 32° C.

When the process has proceeded for a suitable period, as judged by the rate of accumulation of product and concentration of starting material using a technique such as gas chromatography, it may be terminated by any convenient means, for example by removing the micro-organism by centrifugation or filtration and/or by cooling the reaction mass to a temperature of less than 5° C. The process may take a few hours or many days, e.g. 1 hr to 1 week. The product of Formula (2) may be isolated by any convenient means, for example by solvent extraction, preferably using a halocarbon solvent (e.g. CH$_2$Cl$_2$), an aromatic solvent (e.g. toluene) or an ester (e.g. ethyl acetate). The product of the process may be further purified, for example by recrystallisation or chromatography, especially by preparative thin layer chromatography (TLC) using silica gel and a liquid eluent, e.g. an ether, an alkane or a mixture thereof.

According to a second feature of the present invention there is provided a process for the conversion of a compound of Formula (2) into a compound of Formula (3):

Formula (3)

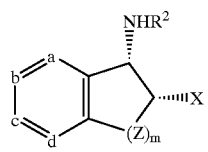

in which R$^2$ is —H or —COR and a, b, c, d, R, X, Z and m are as hereinbefore defined, by reaction of the compound of Formula (2) with an organonitrile compound in the presence of an acid, preferably wherein the absolute configuration is retained at the 1-position. When X is OH, —NH$_2$, SH, Cl, Br or —NHR (wherein R is as hereinbefore defined) the process proceeds well with retention of the absolute configuration at the 1-position, and this can also occur when X is one of the other substituents mentioned above depending on the nature of the compound and the conditions used.

The organonitrile compound is preferably an alkyl, aryl or aralkyl nitrile. When the organonitrile is an alkyl nitrile it is preferably a C$_{1-6}$-alkylnitrile, more preferably a C$_{1-4}$-alkylnitrile and especially acetonitrile. The acid may be an inorganic acid, for example sulphuric, hydrochloric, nitric or phosphoric acids, or an organic acid, e.g. a sulphonic acid, especially methane- or tolyl sulphonic acid. The acid is preferably an inorganic acid, especially sulphuric acid.

The reaction may be performed in a liquid medium and is preferably carried out in the organonitrile compound. Preferably the compound of Formula (2) has been prepared by the process described in the first aspect of the invention.

The process for conversion of (2) into (3) is preferably performed at a temperature from –10° C. to 100° C., more preferably at a temperature from –5° C. to 70° C. and especially at a temperature from –5° C. to 25° C.

The product of Formula (3) may be isolated from the reaction mixture by any convenient means such as by pouring into ice-water, neutralising with an inorganic base such as aqueous sodium hydroxide and extracting with a water-imiscible organic solvent, for example a halocarbon solvent (e.g. CH$_2$Cl$_2$), an aromatic solvent (e.g. toluene) or an ester (e.g. ethyl acetate). The product of Formula (3) may be purified by chromatography or recrystallisation if desired, e.g. recrystallisation from an ester or ketone, e.g. ethyl acetate or pentanone.

According to a further feature of the present invention there is provided a process for the conversion of a compound of Formula (3) in which R$^2$ is —COR and R is as hereinbefore defined into a compound of Formula (3) in which R$^2$ is —H, preferably using a base. Preferably the compound of Formula (3) has been prepared by the process of the second aspect of the invention.

The base is preferably an alkali metal hydroxide, more preferably potassium hydroxide, and especially an aqueous solution of potassium hydroxide. Preferred aqueous solutions comprise from 1% to 50% by weight of base in water, more preferably from 1% to 20%. The reaction is preferably performed at a temperature from 20° C. to 150° C., more preferably at the reflux temperature of the aqueous solution of base. The product may be isolated from the reaction mixture by any convenient means such as salting out or extraction with a water-miscible organic solvent, preferably an ester such as ethyl acetate. The product may be purified by crystallisation from a liquid medium, for example from an alkane such as hexane.

According to a further feature of the present invention there is provided a process for the preparation of a compound of Formula (3) in which R$^2$ is —H which comprises the steps:

i) conversion of a compound of Formula (1) into a compound of Formula (2) using a dioxygenase enzyme, preferably using a *Pseudomonas putida* micro-organism;

ii) conversion of the compound of Formula (2) into a compound of Formula (3) (preferably with retention of the absolute configuration at the 1-position) wherein R$^2$ is —COR, preferably by reaction of the compound of Formula (2) with an organonitrile compound in the presence of an acid; and iii) conversion of the compound of Formula (3) in which $R^2$ is —COR into a compound of Formula (3) in which $R^2$ is —H, preferably using a base;

wherein the compounds of Formula (1), (2) and (3) are as hereinbefore defined.

The present process allows compounds of Formulae (2) and (3) to be prepared in high enantiomeric excess (ee), usually exceeding 85% or even exceeding 95%.

Preferences for a, b, c, d, Y, X, m, R, $R^1$ and Z are as described in relation to the first aspect of the invention with the exception that X is not OH.

The invention is further illustrated by the following Examples.

EXAMPLE 1

Biotransformation of 2-indanol (by *Pseudomonas Putida* UV4)

i) Source of Micro-organism

*Pseudomonas putida* UV4 is a mutant organism derived from *Pseudomonas putida* NCIMB 11767 (NCIMB is The National Collection of Industrial and Marine Bacteria Ltd, 23 St. Macher Drive, Aberdeen, UK, AB2 IRY). Preparation of *Pseudomonas putida* UV4 is described in EP 0 253 485 B1, page 4 line 55 to page 5, line 41 (Mutant strain D), which is incorporated herein by reference thereto.

ii) Growth of *Pseudomonas putida* UV4

*Pseudomonas putida* UV4 was maintained on minimal salts agar plates with sodium pyruvate as carbon source. The minimal salts medium comprised Solution A: 2 g $KH_2PO_4$ 2 $cm^3$ Vishniac trace elements Dissolved in 800 $cm^3$ of distilled water and adjusted to pH 7.0.

Solution B: 3 g $NH_4Cl$ 0.4 g $MgSO_4.7H_2O$

Dissolved in 200 $cm^3$ of distilled water.

Mix 4 parts solution A to 1 part solution B.

The Vishniac trace elements solution was prepared as follows:

50 g EDTA was dissolved in 750 $cm^3$ of distilled water, and adjusted to a pH value of 8.0 with 2M KOH.

The other components were then dissolved in the following order:

2.20 g $ZnSO_4.7H_2O$ 5.54g $CaCl_2$ 5.06 g $MnCl_2.7H_2O$ 5.00g $FeSO_4.7H_2O$ 1.10g $(NH_4)_6Mo_7O_{24}.4H_2O$ 1.57g $CuSO_4.5H_2O$ 1.61g $CoCl_2.6H_2O$

The final pH was adjusted to a value of 6.0, and the volume made up to 1 litre, and then stored at 4° C. in the dark.

Minimal salts agar plates were prepared as follows:

8 g Bacto agar and 400 $cm^3$ solution A into a 500 ml bottle.

100 $cm^3$ solution B into a 150 ml bottle.

20 $cm^3$ 12.5% sodium pyruvate solution into a 50 $cm^3$ bottle.

The three bottles were autoclaved at 121° C., 15psi for 15 minutes. The bottles were allowed to cool, then B and the sodium pyruvate was added to A and poured into petri dish plates. The plates were allowed to set and then stored at 4° C.

Before use, the plates were dried in a UV light drying cabinet.

A single colony was used to inoculate a 250 $cm^3$ flask containing 50 $cm^3$ of minimal salts medium and 2 $cm^3$ 12.5% sodium pyruvate as carbon source. The cells were grown in batch culture at 30° C. on an orbital shaker for approximately 12 hours and were then used to inoculate a 2 litre flask containing 500 $cm^3$ of minimal salts medium and 20 $cm^3$ 12.5% sodium gluconate as carbon source.

After approximately 12 hours growth the 2 litre flask was used to inoculate a 10 litre fermenter (working volume=7.8 litres) which contained: (in 7 litres water) 35 g D-Glucose.

14 $cm^3$ Vishniac trace elements solution.

14 g $KH_2PO_4$ 14 g $NH_4Cl$ 2.8 g $MgSO_4.7H_2O$

The cells were grown for approximately 12 hours with the temperature controlled at 30° C. and pH controlled at 7.2. A 3% solution of polypropylene glycol (PPG) was used as an antifoam and was added when necessary to minimise foam level.

iii) Biotransformation

When the cell density in the fermenter had reached an optical density (at 600 nm) of between 4 and 5 a glucose minimal salts medium (GMS) was added continuously to maintain a set $dO_2\%$ level of between 20 and 80%. The GMS consisted of: (in 1 litre water)

75 g D-Glucose 2 g $KH_2PO_4$

2 $cm^3$ Vishniac trace elements solution 3 g $HN_4Cl$ 0.4 g $MgSO_4.7H_2O$ 0.5g $(NH_4)_2SO_4FeSO_4.6H_2O$ Small aliquots of 2-Indanol (13.5 g/hour for 8 hours) were injected into the broth at regular intervals when the dO2% had returned to its set level.

The broth was harvested and the cells removed by centrifugation at 10000 rpm for 11 minutes at 4° C. The remaining supernatant was stored at 4° C.

The crude product was extracted from the culture medium with ethyl acetate, evaporation of the ethyl acetate gave (−)-cis-(1S,2R)-1,2-dihydroxyindan (50 g, 41%) which was separated from other metabolites and starting material by preparative thin layer chromatography (TLC) using silica gel as separating medium and a mixture of 40% diethylether/ 60% petroleum ether (b.p. 40–60° C.) as eluent. The product had an $[\alpha]_D$=of 48°. The optical purity was determined to be >98% ee (enantiomeric excess) by comparison of the $[\alpha]_D$ with that of optically pure material, and by the MTPA method described in Tet.Lett. 1992, 33, 1241.

EXAMPLE 2

Biotransformation of 2-indanol (by *Pseudomonas putida* NCIMB 8859)

i) Source of Micro-organism

*Pseudomonas putida* NCIMB 8859 was obtained as a freeze-dried culture from The National Collections of Industrial and Marine Bacteria Ltd., 23 St. Macher Drive, Aberdeen, Scotland AB2 1RY.

ii) Growth of *Pseudomonas putida* NCIMB 8859

Cultures were grown on minimal salts agar plates with the addition of naphthalene onto the lid and subcultured at regular intervals to maintain viability. The growth of *Pseudomonas putida* NCIMB 8859 follows that of *Pseudomonas putida* UV4, with the exception of:

2 g/litre naphthalene was used instead of 12.5% sodium pyruvate in the minimal salts agar plates and in the 250 cm³ shake flask.

iii) Biotransformation

When the micro-organism of step ii) had been grown in the 250 cm³ shake flask for 12 hours at 30° C., 2-Indanol (0.1 g) was added along with D-glucose (6 g) and shaking of the flask was continued for a further 4 hours.

The crude product was extracted and purified as in Example 1, stage iii) above, to give (−)-cis-(1S, 2R)-1,2-dihydroxyindan (10 mg).

EXAMPLES 3 to 7

Preparation of cis-(1S, 2R)-2-substituted indan-1-ols

The procedure of Example 1 was repeated except that in place of 2-indanol there was used the substrate shown in the second column to give the product shown in the third column. Yield and characterising data are shown in the final column.

Sulphuric acid (2.9 ml, 18M, 52.48 mmol) was added slowly (1 hour) to (−)-cis −(1S,2R)-1,2-dihydroxyindan (0.5 g, 3.35 mmol) in acetonitrile (10.2 ml) at −5° C. The reaction mixture was allowed to warm to room temperature and stirred overnight. The reaction mixture was quenched into ice/ethylacetate 1:1 (20 ml) and the pH adjusted to 7 using sodium hydroxide solution.

The aqueous and organic phases were separated and salt was added to the lower aqueous layer before extraction with ethyl acetate (3×50 ml).

The combined organic phases were dried over anhydrous MgSO₄ and reduced in volume to about 15 ml. The product crystallised spontaneously and was collected by filtration to give (−)-cis-(1S,2R)-1-acetamido-2-hydroxyindan (600 mg, 70%) m.p. 165–166° C., [α]$_D$+45°(CHCl₃).

| Example No | Substrate | Product | Data |
|---|---|---|---|
| 3 | 2-acetoxyindan | ![structure] | 41% yield<br>>98% ee |
| 4 | 2-bromoindan | ![structure] | 35% yield<br>>98% ee mp 110° C.<br>[α]$_D$ = 61° |
| 5 | 2-methylindan | ![structure] | 27% yield<br>>98% ee mp 51–52° C. [α]$_D$ = 38° |
| 6 | 2-chloroindan | ![structure] | 90% yield<br>>99% ee mp 109° C.<br>[α]$_D$ = 52° |
| 7 | 2-azidoindan | ![structure] | 61% yield<br>mp 149–150° C.<br>[α]$_D$ = 104° |

Example 8

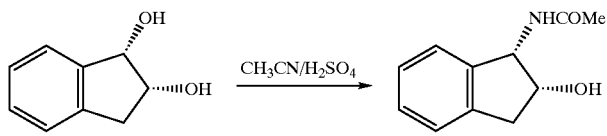

EXAMPLE 9

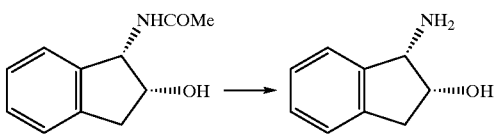

The product from Example 8 (0.1 g, 0.52 mmol) was heated under reflux with potassium hydroxide (10 cm$^3$, 10% w/v) for 8 hours. The amine product was isolated by saturation of the aqueous solution with sodium chloride followed by extraction with ethyl acetate (3×15 cm$^3$) The combined extracts were dried over magnesium sulphate and the solvent was removed in vacuo to yield the crude 1-amino-2-hydroxy indan which was re-crystallised from ethyl acetate/hexane.

Yield 0.068 g (88%), m.p. 116–117° C., $[\alpha]_D$-64° (CHCl$_3$).

We claim:

1. A process for conversion of a compound of the Formula (1):

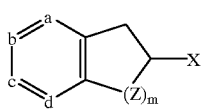

Formula (1)

into a compound of the Formula (2):

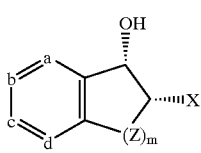

Formula (2)

comprising contacting a dioxygenase enzyme with a compound of Formula (1) and recovering the resulting compound of Formula (2);

wherein:
  a, b, c and d are each independently selected from CH and CY, or one of a, b, c and d is a nitrogen atom and all of the others are selected from CH and CY;
  X and Y each independently is selected from the group consisting of alkyl, —OH, —OR, —OCOR, —SH, —SR, —F, —Cl, —Br, —I, —NH$_2$, —NHR, —NRR$^1$, —NHCOR, —NRCOR$^1$, —CN, —COOR, —COOH, —COR, —CONH$_2$, —CONHR, —CONRR$^1$, —NO$_2$, —N$_3$, —PRR$^1$, —P(O)RR$^1$, —P(O)(OH)$_2$, —P(O)(OROH), —P(O)OROR$^1$, —S(O)R, —SO$_2$R, —SO$_2$H or —SO$_3$H;
  Z is CH$_2$, CHR, CRR$^1$, O, NH, NR, S, C=O or CHX;
  R and R$^1$ are each independently alkyl, aryl or aralkyl; and
  m has a value of from 0 to 4.

2. A process according to claim 1 wherein the dioxygenase enzyme is present in whole cells.

3. A process according to claim 1 wherein said dioxygenase enzyme is in a *Pseudomonas putida* micro organism.

4. A process according to any one of claims 1 to 3 wherein a, b, c and d are all CH.

5. A process according to any one of claims 1 to 3 wherein Z is CH$_2$ and m is 1 or 2.

6. A process according to any one of claims 1 to 3 which is performed in a liquid medium at a pH in the range 6 to 8.

7. A process according to any one of claims 1 to 3 wherein the compound of Formula (1) is 2-indanol, 2-acetoxyindan, 2-bromoindan, 2-methylindan, 2-chloroindan or 2-azidoindan.

8. A process for conversion of a compound of Formula (2) into a compound of Formula (3):

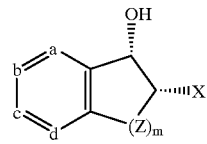

Formula (2)

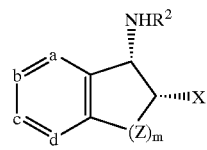

Formula (3)

wherein R$^2$ is H or —COR; a, b, c and d are each independently selected from CH and CY, or one of a, b, c and d is a nitrogen atom and all of the others are selected from CH and CY; Z is CH$_2$, CHR, CRR$^1$, O, NH, NR, S, C=O or CHX; each R and R$^1$ are each independently alkyl, aryl or aralkyl; m has a value of from 0 to 4; and X and each Y independently is selected from the group consisting of alkyl —OH, —OR, —OCOR, —SH, —SR, —F, —Cl, —Br, —I, —NH$_2$, —NHR, —NRR$^1$, —NHCOR, —NRCOR$^1$, —CN, —COOR, —COOH, —COR, —CONH$_2$, —CONHR, —CONRR$^1$, —NO$_2$, N$_3$, —PRR$^1$, —P(O)RR$^1$, —P(O)(OH)$_2$, —P(O)(OROH), —P(O)OROR$^1$, —S(O)R, —SO$_2$R —SO$_2$H or —SO$_3$H; which comprises (a) preparing the compound of Formula (2) by a process according to claim 1 and (b) reacting the compound of Formula (2) with an organonitrile compound in the presence of an acid and recovering the compound of Formula (3).

9. A process for preparing a compound of Formula (3) in which R$^2$ is H;

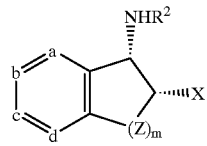

Formula (3)

which comprises the steps:

i) contacting of a compound of Formula (1) with a dioxygenase enzyme to obtain a compound of Formula (2);

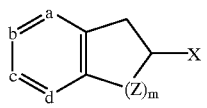

Formula (1)

-continued
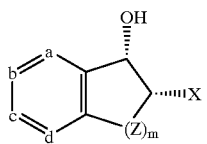
Formula (2)
ii) reacting the compound of Formula (2) with an organonitrile compound in the presence of acid to produce a compound of Formula (3) wherein $R^2$ is —COR; and
iii) reacting the compound of Formula (3) in which $R^2$ is —COR with a base to produce a compound of Formula (3) in which $R^2$ is —H;
wherein R, a, b, c, d, Z, m and X are as defined in claim 1.
* * * * *